United States Patent [19]

McWhorter

[11] 4,106,509
[45] Aug. 15, 1978

[54] CATHETERS

[75] Inventor: Daniel M. McWhorter, Arlington Heights, Ill.

[73] Assignee: The Kendall Company, Boston, Mass.

[21] Appl. No.: 711,774

[22] Filed: Aug. 5, 1976

[51] Int. Cl.² .......................................... A61M 25/00
[52] U.S. Cl. ............................................... 128/349 B
[58] Field of Search .................... 128/348, 349, 349 B, 128/349 BV, 350 V, 351, 295

[56] References Cited

U.S. PATENT DOCUMENTS

| 3,429,314 | 2/1969 | Ericson | 128/349 R |
| 3,547,126 | 12/1970 | Birtwell | 128/349 B |
| 3,815,608 | 6/1974 | Spinosa et al. | 128/350 R X |
| 3,820,546 | 6/1974 | Chittenden et al. | 128/349 R |

OTHER PUBLICATIONS

Plastic World, Jul. 1971.

Amer. Jour. Surg., vol. 100, Oct. 1960, "Cantor", pp. 584–586.

Primary Examiner—Dalton L. Truluck

[57] ABSTRACT

A drainage system including a balloon catheter comprising a tubular shaft having proximal and distal ends, an inflatable sleeve surrounding the shaft adjacent the distal end thereof and upon inflation retaining the catheter in position by formation of an enlarged balloon surrounding the shaft, a first opening adjacent the distal end of the shaft through which body fluids may pass into a drainage channel which extends from the first opening through the length of the shaft, and a second opening spaced from the first opening through which the fluids may pass from the channel. A longitudinally extending portion of the channel is formed from a porous material which is pervious to air and impervious to body fluids and which is not-wettable by body fluids, and the inflatable sleeve comprises an elastomeric material other than the porous material.

8 Claims, 6 Drawing Figures

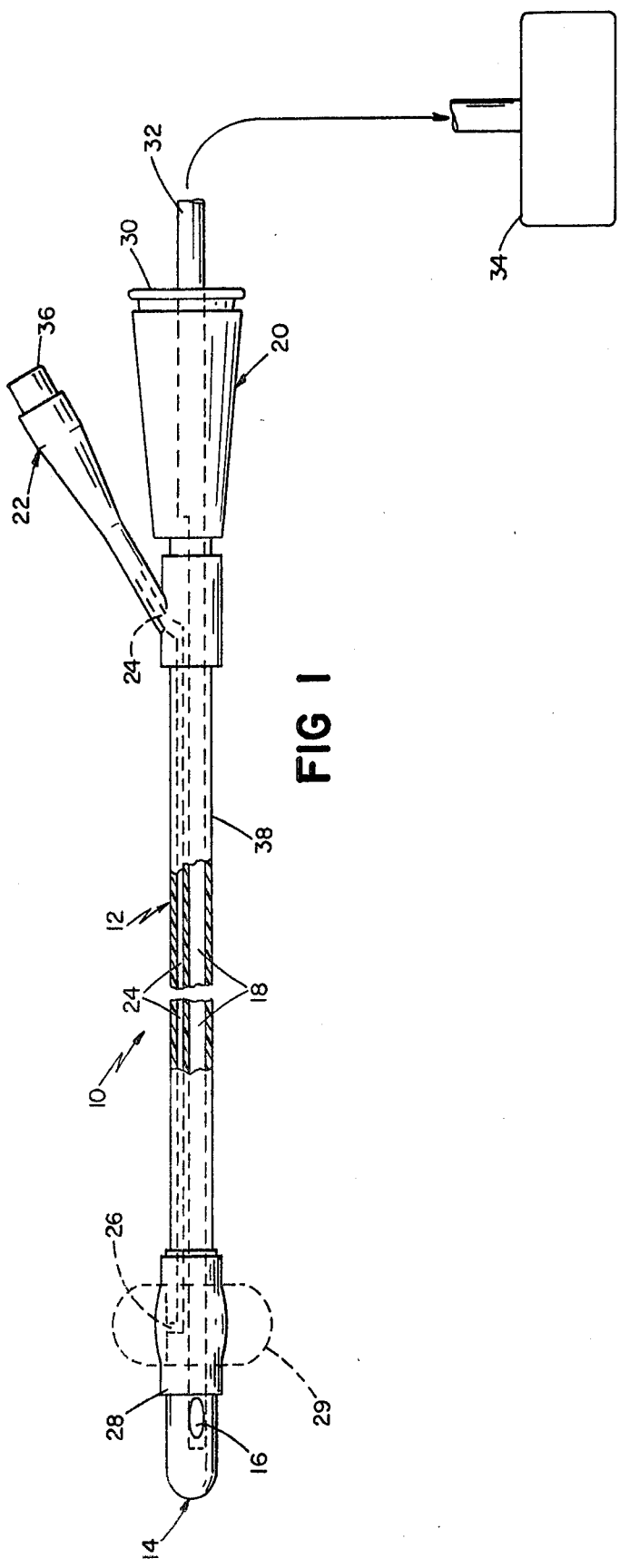
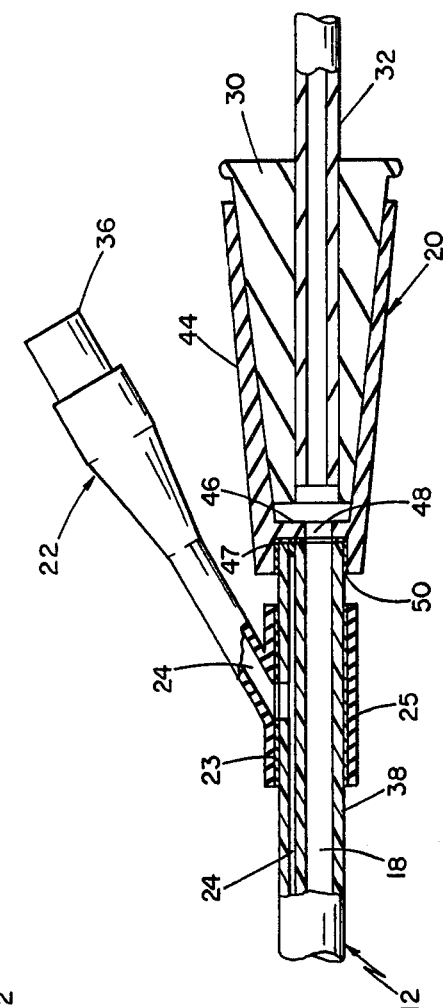
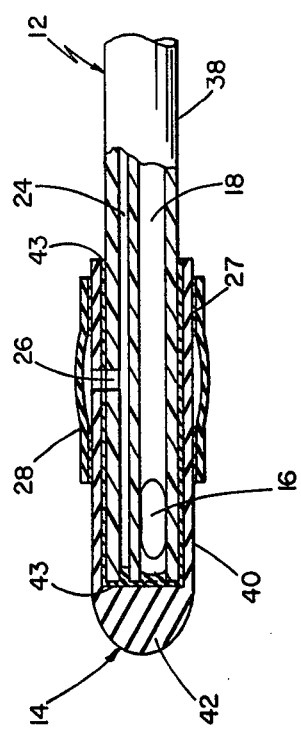
FIG 1
FIG 3
FIG 2

CATHETERS

This invention relates to balloon catheters.

Balloon catheters are used to drain fluids from animal body cavities, and are often left within an animal for a considerable period of time. A problem arises when the fluid draining through the catheter creates a suction in the catheter drainage tube. This suction persists after fluid has been exhausted from within the body cavity and portions of the body cavity walls are drawn into orifices of the catheter, thus causing trauma and possible rupture of the body cavity wall. Disruption of such protective tissue creates possible portals of entry for invading microorganisms.

The suction may be eliminated and the traumatic effects of suction avoided by permitting air to enter the drainage tubes, and U.S. Pat. Nos. 3,429,314 and 3,419,009 disclose catheters including vacuum breaking devices designed to permit such air flow. Since entering air should be bacteria-free to avoid introduction of bacteria into the body, and the body fluids should not leak out, the known vacuum breaking devices have included a bacterial filter and are liquid impervious.

Worthwhile as the devices disclosed in the aforementioned patents are, they nevertheless have drawbacks. One drawback is that incorporation of the vacuum breaking devices they disclose often requires major modification of the overall structure of the catheter. A second drawback is that the air-flow and filter area of the vacuum-breaking devices is quite small.

Primary objects of the present invention are to provide balloon catheters having vacuum breaking systems which eliminate the need for major modification of normal catheter configuration, and in which a portion of the drainage tube itself provides a large air flow area. Other objects include providing balloon catheters which more efficiently break negative pressure build-ups, which have reduced tissue reactivity and, in some embodiments, in which separately attached vacuum-breaking elements are unnecessary.

The invention features, in a drainage system including a balloon catheter comprising a tubular shaft having proximal and distal ends, an inflatable sleeve surrounding the shaft adjacent the distal end thereof and upon inflation retaining the catheter in position by formation of an enlarged balloon surrounding the shaft, a first opening adjacent the distal end of the shaft through which body fluids may pass into a drainage channel which extends from the first opening through the length of the shaft, and a second opening spaced from the first opening through which the fluids may pass from the channel, those improvements wherein at least a longitudinally extending portion of the channel is formed from a porous material which is pervious to air and impervious to body fluids and which is not-wettable by body fluids, and wherein the inflatable sleeve comprises an elastomeric material other than the porous material.

Preferred embodiments including a connector of elastomeric material other than the porous material feature a porous polytetrafluoroethylene whose pores have a maximum pore size of not greater than about 5 (preferably about 0.7) microns forming the full length catheter main shaft, a sleeve and connector are bonded directly to the shaft, and, optionally, either tubing extending from the connector to a collector or an adapter between the connector and such tubing comprising the porous material.

Other objects, features, and advantages will appear from the following detailed description of preferred embodiments thereof, taken together with the attached drawings in which:

FIG. 1 illustrates a drainage system including a balloon catheter constructed in accordance with the present invention;

FIGS. 2 and 3 illustrate portions of FIG. 1 in partial cross section;

Figure 5:
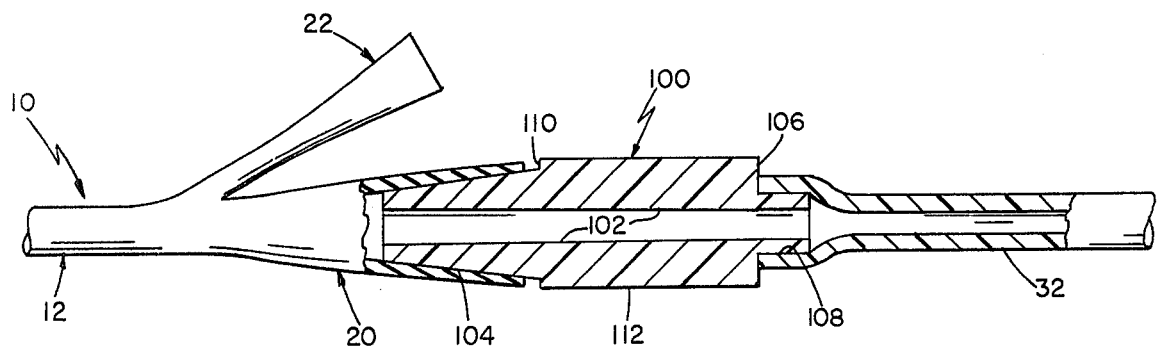
FIG. 5 illustrates an adapter for use, inter alia, with the catheter of FIG. 1; and, FIG. 6 illustrates a drainage tube for use, inter alia, with the catheter of FIG. 1.

Referring more particularly to the drawings, FIGS. 1-3 illustrate a drainage system including a balloon retention catheter 10. The catheter has a flexible insertion main arm 12 which terminates at one end (the distal end) in a tip 14 containing a drainage eye or orifice 16. The drainage eye extends through the tip and intersects the main drainage lumen 18. Drainage lumen 18 extends from the intersection with eye 16 through the length of main arm 12 to a connection bell 20 at the end thereof (the proximal end) opposite tip 14. A side arm 22 is attached to the main arm 12 adjacent its proximal end. An inflation lumen 24 extends from within side arm 22, into main arm 12 and along the interior of main arm 12, to an opening 26 through the main arm wall. An inflatable bag 28 is sealed circumferentially around the portion of main arm 12 including opening 26.

A tapered hollow thermoplastic adapter 30 is inserted into bell 20, and a flexible drainage tube 32 extends from within adapter 30 to a drainbox 34. In use, body fluids flow into the distal end of catheter 10 through drainage eye 16, and then flow through catheter drainage lumen 18 and tube 32 (which together with the central bore of adapter 30 comprise the system's drainage channel) to the collection vessel 34 where they are collected.

Catheter 10 is retained in place in a body cavity using a retention system similar to that of an ordinary Foley-type catheter. A combination stopper and inflation plug 36 is provided at the end of side arm 22. A hypodermic needle and syringe may be inserted through plug 36 and fluid, typically water, forced into the side arm, and thence through inflation lumen 24, to inflate bag 28 to the expanded configuration 29 shown in phantom in FIG. 1. Alternatively, plug 36 may have a needleless valve and the fluid may be injected therethrough by a syringe alone. The catheter may also be of the self-inflating type in which side arm 22 includes an inflated reservoir and a clamp for retaining fluid in the reservoir. In the self-inflating type, the side arm reservoir is inflated in the conventional manner, and the clamp is released after the catheter has been inserted in a body cavity. Upon release of the clamp, fluid in the reservoir is forced to flow through inflation lumen 24 into bag 28 by elastomeric contraction of the walls of side arm 22, and inflates the bag to the configuration 29 shown in phantom in FIG. 1. In either type of catheter, air may be used to inflate bag 28 if the inflation lumen 24 is lined with an air-impervious material.

As shown most clearly in FIGS. 2 and 3, main arm 12 comprises an elongated tube 38 to which tip 14, side arm 22 and connection bell 20 have been bonded. Tube 38 is made (typically by extrusion) from any flexible porous material that is pervious to air and impervious to body fluids (and impervious also, unless inflation lumen 24 is lined, to the fluid used to inflate balloon 28), and that is non-wettable by body fluids. One material that has been found to be especially well-suited for use in the present invention is microporous polytetrafluoroethylene, such as that sold by W. L. Gore & Associates of Newark, Delaware under the trademark "Gore-Tex". The material should also be relatively inert and have a low reactivity with the body tissue with which it is in contact. U.S. Pat. No. 3,815,608 discloses a non-balloon catheter and states that Gore-Tex brand polytetrafluoroethylene is useful therein because it is flexible, hydrophobic, and has a very smooth surface which discourages crystallization and has a low coefficient of friction. The microporous material of which 38 is constructed, whether or not polytetrafluoroethylene, should have pores whose maximum size is no greater than about 5 microns. Preferably the maximum pore size should be about 0.7 microns. Pores of such size, in conjunction with the tortuous path the pores define through the tube wall and the non-wettable nature of the material, not only provide the desired air-porosity and liquid-nonporosity, but also act as a bacterial filter.

Tip 14 comprises a thin-walled elastomeric sleeve 40 closed at one end by a solid bulbous and rounded tip portion 42. Sleeve 40 overlies and compressively engages (i.e., is stretched around) the outer cylindrical surface of the distal end portion of tube 38. Tip portion 42 overlies the axial distal end of tube 38, closing off the ends of drainage lumen 18 and inflation lumen 24. In the illustrated preferred embodiment, tip 14 is a unitary piece of elastomeric silicone rubber, and is adhesively bonded to tube 38 by a layer of adhesive 43. In addition to providing a bond between the facing surfaces of the tip and tube, the bonding adhesive 43 flows into and blocks the ends of drainage lumen 18 and inflation lumen 24.

Balloon 28 is similar to the inflation balloons used in conventional catheters. It is elastomeric (in the preferred embodiment, elastomeric silicone rubber) and is bonded, typically by an adhesive layer 27, around the exterior of tip sleeve 40. As shown, opening 26 extends through the side walls of both tube 38 and sleeve 40, to permit fluid flow from inflation lumen 24 into balloon 28.

Connection bell 20 and side arm 22 are made of any suitable non-rigid material, generally other than polytetrafluoroethylene. Typically, they comprise an elastomeric material such as rubber latex or silicone elastomer. Other suitable materials include polyvinylchloride and polyurethane.

As shown in FIG. 3, connection bell 20 includes a generally frustro-conical wall 44 and an internal axial barrier 46 with an axial opening 48 extending therethrough. The adjacent axial end portion of tube 38 is fitted into a cylindrical recess 50 at the smaller diameter end of bell 20, with the axial end face of the tube engaging barrier 46 and drainage lumen 18 communicating with opening 48. The tube and bell are bonded together by adhesive 47, and the adhesive flows slightly into and blocks the end of inflation lumen 24.

Side arm 22 comprises a generally circular in cross-section, flexible tube the smaller diameter end of which defines a sleeve 25 compressively surrounding and bonded by adhesive 23 to the outer surface of main tube 38. A conventional combination stopper plug and inflator valve 36 is fitted into the larger diameter end. In other embodiments, in which the catheter is of the self-inflation type, side arm 22 will be of, or at the least will include a portion which is, an elastomeric material (such as elastomeric silicone rubber) which may be inflated to contain a reservoir of fluid for inflating bag 28.

Figure 4:
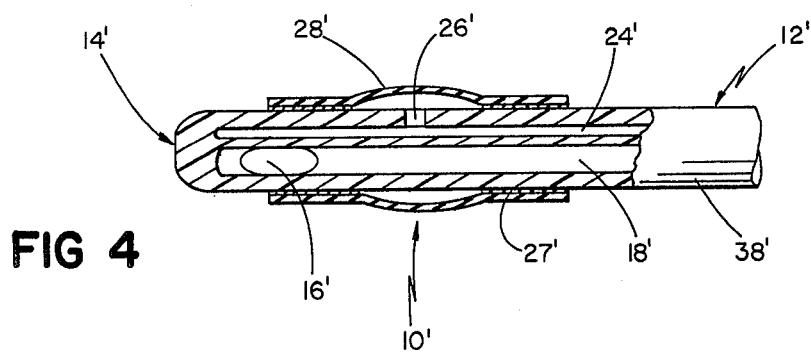
FIG. 4 illustrates a modification of the catheter of FIG. 1.

Reference is now made to FIG. 4, wherein is shown a modified embodiment of the present invention. Many portions of the embodiment of FIG. 4 are substantially identical to corresponding portions of that of FIGS. 1–3 and are identified by the same reference numerals, with a differentiating prime (') added. More specifically, FIG. 4 illustrates the distal end portion of a catheter 10' substantially identical to catheter 10 except for the configuration of tip 14' and inflation balloon 28'. As shown, tip 14' is an integral part of shaft 12', and inflation balloon 28' surrounds and is bonded by adhesive layer 27' directly to the exterior surface of the shaft. The specific configuration of the distal end portion of catheter 10, i.e., an inflation balloon 28 overlying the elongated sleeve 40 of a separate tip 14, forms no part of the present invention.

FIG. 5 illustrates an elongated microporous adapter 100 having one end thereof attached to the connection bell 20 of catheter 10 and the other end thereof attached to drainage tube 32. As shown, adapter 100 comprises a generally cylindrical tube having a bore 102 extending axially through its entire length. One end 104 of adapter 100 is tapered so that its outer surface is in the form of a conical frustum. A cylindrical flange 108 of reduced diameter projects axially from the other end 106. Tapered end 104 is inserted tightly into connection bell 20, and drainage tube 32 is expanded over and fitted tightly around flange 108. The distance adapter 100 may be inserted into connection bell 20 is limited by the increasing diameter of tapered end 104 and, in the illustrated embodiment, by axially-facing step 110 between the conical surface of tapered end 104 and the outer cylindrical surface 112 of the central portion of adapter 100. The distance tube 32 may be fitted over flange 108 limited by the axially-facing surface of end 106. The cylindrical outer surface 112 of adapter 100, between connection bell 20 and drainage tube 32, define an air flow area, having a length equal to the axial distance between step 110 and end 106, through which air may migrate through adapter 100 to bore 102.

Adapter 100 is made from a material, similar to that previously discussed with reference to the microporous material of the embodiment of FIGS. 1–3, that is pervious to air and impervious pervious to and not wetted by body fluids. The maximum size of the pores of the material of adapter 100 generally is less than about 5 microns and, preferably, is about 0.7 microns. The tissue reactivity of the material of which the adapter is made is less important than that of the microporous material of the tube 38 of catheter 10 since the adapter is not in direct and intimate contact with body tissue. Additionally, the adapter is generally rigid or semi-rigid, rather than being flexible as is tube 38 of the previously discussed embodiment. Microporous polytetrafluoroethylene materials sold by W. L. Gore & Associates under the trademark "Gore-Tex" are suitable for making adapter 100.

Figure 6:
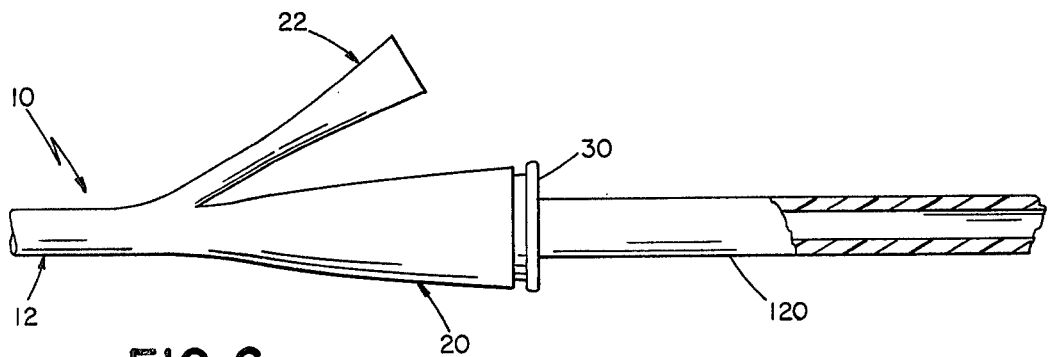

FIG. 6 illustrates a drainage system in which the flexible drainage tube 120 connected to adapter 30 and leading to the collection vessel 34 (not shown in FIG. 6) is made of flexible microporous material. As before, the material is pervious to air, and impervious to and not wetted by body fluids. The pore extending through the wall of tube 120 have a maximum size of about 2 microns and, preferably, their maximum size is about 0.7 microns. In the illustrated embodiment, tube 120 is a flexible polytetrafluoroethylene tube made and sold by W. L. Gore & Associates under the trademark "Gore-Tex".

As will be apparent, microporous adapter 100 and microporous tube 120 each provides for substantial air flow into the drainage channel of a catheter system, thus preventing the buildup of undesirable suction. In the above embodiments, each adapter 100 and microporous tube 120 is used in combination with a catheter 10 itself having a microporous tube 38. Alternatively, both adapter 100 and microporous tube 120 may be used with catheter 10 (by substituting tube 120 for tube 32 in the embodiment of FIG. 5), or either or both adapter 100 and microporous tube 120 may be used with a conventional balloon or Foley-type catheter. If desired, microporous tube 120 may form only a part of the entire drainage tube extending from the catheter to the drain box. In these latter circumstances, the microporous tube 120 should be adjacent, preferably attached directly to, the catheter, and conventional tubing may extend the remaining distance to the collection box.

Other embodiments will be within the scope of the following claims.

What is claimed is:

1. In a drainage system including a hollow catheter comprising a tubular shaft having proximal and distal ends, an inflatable sleeve surrounding the shaft adjacent the distal end thereof and upon inflation retaining the catheter in position by formation of an enlarged balloon surrounding the shaft, a first opening adjacent the distal end of the shaft through which body fluids may pass into a drainage channel defined by the drainage system and extending from the first opening through the length of the shaft, and a second opening spaced from the first opening through which the fluids may pass from the channel, that improvement comprising:
    tubing connected to the proximal end of said catheter, defining a portion of said drainage channel, and having an outlet communicating with a receptacle; at least a longitudinally-extending circular in transverse cross-section portion of said tubing being of a porous material which is pervious to air but impervious to body fluids and which is not-wettable by body fluids, whereby air may pass through said material to said channel.

2. In a drainage system including a balloon catheter comprising a tubular shaft having proximal and distal ends, an inflatable sleeve surrounding the shaft adjacent the distal end thereof and upon inflation retaining the catheter in position by formation of an enlarged balloon surrounding the shaft, a first opening adjacent the distal end of the shaft through which body fluids may pass into a drainage channel defined by the drainage system and extending from the first opening through the length of the shaft, and a second opening spaced from the first opening through which the fluids may pass from the channel, that improvement comprising:
    an adapter having an interior bore defining a portion of said drainage channel, one end of said adapter being attached to said catheter to permit said fluids to flow from said catheter into said bore, another end of said adapter being adapted for connection to tubing extending from said adapter to a receptacle to permit said fluids to flow from said adapter to said receptacle, and said adapter comprising a porous material which is pervious to air but impervious to body fluids and which is not-wettable by body fluids, whereby air may pass through said material to said channel.

3. The catheter of claim 2 wherein said adapter is generally circular in cross-section, said bore extends generally axially through the length of said adapter, and said adapter includes three axially-spaced, generally radially-facing surfaces, a first one of said surfaces being adapted for engaging said catheter, a second one of said surfaces being adapted for engaging said tubing, and the third one of said surfaces being intermediate said first one and said second one and defining an air-flow surface of predetermined minimum axial length.

4. The catheter of claim 3 including respective axial steps intermediate said first one and said third one surfaces and intermediate said third one and said second one surfaces.

5. The catheter of claim 4 wherein each of said surfaces is generally outwardly-facing.

6. The catheter of claim 2 wherein said porous material is a porous polytetrafluoroethylene.

7. The catheter of claim 2 wherein said porous material comprises pores having a predetermined maximum pore size not greater than about 5 microns.

8. The catheter of claim 7 wherein said predetermined maximum pore size is about 0.7 microns.

* * * * *